United States Patent [19]
Davis et al.

[11] Patent Number: 6,093,716
[45] Date of Patent: Jul. 25, 2000

[54] SUBSTITUTED 2-PYRIMIDINEAMINES AND PROCESSES FOR THEIR PREPARATION

[75] Inventors: Peter David Davis, Aston Rowant; David Festus Charles Moffat, Maidenhead; Mark James Batchelor, Cumnor Hill, all of United Kingdom

[73] Assignee: Celltech Therapeutics, Limited, Slough, United Kingdom

[21] Appl. No.: 08/931,271

[22] Filed: Sep. 15, 1997

[30] Foreign Application Priority Data

Sep. 16, 1996 [GB] United Kingdom .................... 9619284

[51] Int. Cl.[7] ...................... A61K 31/505; C07D 401/12; C07D 401/14; C07D 403/14
[52] U.S. Cl. .......................... 514/253; 544/295; 544/298; 544/331; 514/252; 514/272; 514/275
[58] Field of Search ...................................... 544/330–331, 544/332, 295, 298; 514/272, 275, 252, 253

[56] References Cited

U.S. PATENT DOCUMENTS

| | | | |
|---|---|---|---|
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1989 | Schmiechen et al. | 548/517 |
| 4,303,649 | 12/1981 | Jones | 514/8 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |

(List continued on next page.)

FOREIGN PATENT DOCUMENTS

| | | |
|---|---|---|
| 0 233 461 A2 | 8/1987 | European Pat. Off. . |
| 0233461 | 8/1987 | European Pat. Off. . |
| 0295210 | 12/1988 | European Pat. Off. . |
| 0337943 | 10/1989 | European Pat. Off. . |
| 0393500 | 10/1990 | European Pat. Off. . |
| 0490823 | 6/1991 | European Pat. Off. . |
| 0470805 | 2/1992 | European Pat. Off. . |
| 0497564 | 8/1992 | European Pat. Off. . |
| 0511865 | 11/1992 | European Pat. Off. . |
| 0537742 | 4/1993 | European Pat. Off. . |
| 0564409 | 10/1993 | European Pat. Off. . |
| 2 545 345 A1 | 11/1984 | France . |
| 250 1443 | 7/1975 | Germany . |
| 3-77872 | 4/1991 | Japan . |
| 3-77923 | 4/1991 | Japan . |
| 1588639 | 4/1981 | United Kingdom . |
| WO 87/06576 | 11/1987 | WIPO . |
| WO 91/15451 | 10/1991 | WIPO . |
| WO 91/16892 | 11/1991 | WIPO . |
| WO 92/00968 | 1/1992 | WIPO . |
| WO 92/06085 | 4/1992 | WIPO . |
| WO 92/06963 | 4/1992 | WIPO . |
| WO 92/07567 | 5/1992 | WIPO . |
| WO 92/12961 | 8/1992 | WIPO . |
| WO 92/19594 | 11/1992 | WIPO . |
| WO 92/19602 | 11/1992 | WIPO . |
| WO 93/10118 | 5/1993 | WIPO . |
| WO 93/19748 | 10/1993 | WIPO . |
| WO 94/02465 | 2/1994 | WIPO . |
| WO 94/10118 | 5/1994 | WIPO . |
| WO 94/12461 | 6/1994 | WIPO . |
| WO 94/13661 | 6/1994 | WIPO . |
| WO 94/14742 | 7/1994 | WIPO . |
| WO 94/20446 | 9/1994 | WIPO . |
| WO 94/20455 | 9/1994 | WIPO . |
| WO 95/04046 | 2/1995 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 95/17386 | 6/1995 | WIPO . |
| WO 95/31451 | 11/1995 | WIPO . |
| WO 95/33727 | 12/1995 | WIPO . |
| WO 95/35281 | 12/1995 | WIPO . |
| WO 95/35283 | 12/1995 | WIPO . |
| WO 96/14843 | 5/1996 | WIPO . |
| WO 97/09297 | 3/1997 | WIPO . |

OTHER PUBLICATIONS

Chemical Abstracts, Registry No. 2732–15–2, prior to 1967.
Chemical Abstracts, Registry No. 4593–13–9, prior to 1967.

(List continued on next page.)

*Primary Examiner*—Mukund J. Shah
*Assistant Examiner*—Ann M. Kessinger
*Attorney, Agent, or Firm*—Woodcock Washburn Kurtz MacKiewicz & Norris LLP

[57] ABSTRACT

Compounds of general formula (1):

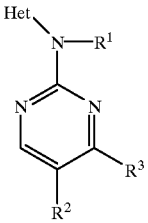

(1)

are described wherein Het is an optionally substituted heteroaromatic group; $R^1$ is a hydrogen atom or a straight or branched chain alkyl group; $R^2$ is a hydrogen or halogen atom or a group —$X^1$—$R^{2a}$ where $X^1$ is a direct bond or a linker atom or group, and $R^{2a}$ is an optionally substituted straight or branched chain alkyl, alkenyl or alkynyl group; $R^3$ is an optionally substituted aromatic or heteroaromatic group; and the salts, solvates, hydrates and N-oxides thereof. The compounds are selective protein kinase inhibitors, particularly the kinases $p56^{lck}$, ZAP-70 and protein kinase C and are of use in the prophylaxis and treatment of immune diseases, hyperproliferative disorders and other diseases in which inappropriate protein kinase action is believed to have a role.

7 Claims, No Drawings

U.S. PATENT DOCUMENTS

| | | | |
|---|---|---|---|
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow | 514/336 |
| 5,693,659 | 12/1997 | Head et al. | 514/357 |
| 5,723,460 | 3/1998 | Warrellow et al. | 514/247 |
| 5,728,708 | 3/1998 | Zimmermann | 514/275 |
| 5,739,144 | 4/1998 | Warrellow et al. | 514/277 |
| 5,753,663 | 5/1998 | Flippin et al. | 514/257 |

OTHER PUBLICATIONS

Bortolus et al., "cis–trans Isomerization of azastilbenes photosensitized by biacetyl", *Mol. Photochem.*, 1970, 2(4), 311–321, CAPLUS accession No. 1971–434722.

Kaiser et al., "Selective metalations of methylated pyridines and quinolines", *J. Org. Chem.*, 1973, 38(1), 71–75, CAPLUS accession No. 1973–71853.

Kefalas, P. et al., "Signalling by the p60$^{c-src}$ Family of Protein–Tyrosine Kinases", *Int. J. Biochem. Cell Biol.*, 1995, 27(6), 551–563.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll. Sci. Fac. Chim. Ind. Bologna*, 1966, 24(2–3), 75–91.

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39(26), 5027–5030.

Lehmann, J. et al., "Lactones; XIII. Grignard Reaction Followed by Phase–Transfer Oxidation: A Convenient Synthesis of γ, γ–Distributed γ–Butyrolactones from γ–Butyrolactone", *Synthesis*, 1987, 1064–1067.

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Chemical Abstracts, "Hypoglycemic Pharmaceuticals Containing Manzammide Derivatives", *Chem. Abstr.*, 1983, 99(6), No. 43558Z.

Dent et al., "Inhibition of eosinophil cyclic nucleotide PDE activity and opsonised zymosan–stimulated respiratory burst by 'type IV'–selective PDE inhibitors", *Br. J. Pharmacol.*, 1991, 103, 1339–1346.

Grammaticakis, "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin DeLa Societa Chemique De France*, 1965, 848–858.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Karlsson et al., "T–Lymphocyte and Inflammatory Cell Research in Asthma", Joller, G. et al. (eds.), Academic Press, 1993, 323–347.

Mathison et al., "Synthesis and Hypotensive Properties of Tetrahydroixoquinolines", *J. Med. Chem.*, 1973, 16(4), 332–336.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 125577y.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.*, 1990, 27, 647–660.

Trost and Fleming (eds.), *Comprehensive Organic Synthesis*, Pergamon Press, New York, 1991, 3, 531–541.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, 1993, 58, 4791–4793.

Pickett, W.C. et al., "Modulation of Eicosanoid Biosynthesis by Novel Pyridinylpyrimidines", *Ann. N.Y. Acad. Sci.*, 1994, 744, 299–305.

Spada, A.P. et al., "Small Molecule Inhibitors of Tyrosine Kinase Activity", *Exp. Opin. Ther. Patents*, 1995, 5(8), 805–817.

Yamaguchi, H., "Guanidinobenzene derivatives as anticoagulants", *Chem. Absts.*, 1989, 110, 655 (Abstract No. 94706z).

Zimmermann, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmermann, J. et al., "Phenylamino–Pyrimidine (PAP)—Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.*, 1997, 7(2), 187–192.

Ashton, "Selective Type IV Phosphodiesterase Inhibitors as Antiasthmatic Agents. The Synthesis and Biological Activities of 3–(Cyclopentyloxy)–4 methyoxybenzamides and Analogues", *J. Med. Chem.*, 1994, 37, 1696–1703.

Beavo & Reifsnyder, "Primary Sequence of cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. of Organic Chemistry*, 1958, 1261–1263.

Buu–Hoi et al., "New Method for the Synthesis of w,w–Diarylacetophenones Aminated in the Aromatic Nucleus. Plynitration of Triarylethylenes", *Chem. Abstr..*, 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chemical Abstracts. Registry Handbook –Number Section. Printed Issues Columbus US *compounds with registry numbers 95992–21–5; 95971–60–1; 90053–37–5; 82668–18–6;80395–25–1; 49610–49–3.

Daves, G.D. et al., "Pyrimidines. XIII. 2–and 6–Substituted 4–Pyrimidinecarboxylic Acids", *J. Of Hev. Chem.*, 1964, 1, 130–133.

Dietl. F. et al., "Chinone von Benzo–und Dibenzokronenethern", *Synthesis*, 1985, 626–631.

El–Wakil et al., "Study of the proton magnetic resonance of methoxytamoxifen towards ortho–substitiution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Hanks, S.K. et al., "The eukaryotic protein kinase superfamily: kinase (catalytic) domain structure and classification", *FASEB J.*, 1995, 9, 576–596.

Hirose et al., "Styrene Derivatives and Electrophotpgraphic Photoreceptor Containing Them", *Chem. Abstr.*, 1993, 118, 136183z.

Ishikura, M. et al., "AN Efficient Synthesis of 3–Heteroarylpyridines via Diethyl–(3–pyridyl) –borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Lisle, H. et al., "IL–2–Induced Eosinophilia in the Rat Pleural Cavity: The Effect of Dexamethasone and Indomethacin", *J. Pharmacol.*, 1993, 108, 230.

Livi et al., "Cloning and Expression of cDNA for a Human Low–$K_m3$ Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents(1)" *J. Heterocyclic Chem.*, 1979, 16, 711–715.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic system. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphospine in Synthesis and Transformation and Triphenylphosphine in Synthesis and Transformation of Natural Products" *Synthesis*, 1981, 1–28.

Newton, A.C. "Protein Kinase C: Structure, Function Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the AUrone Derivatives at the Conventiona Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed *Ortho*–Lithiation of Fluoropyrimidines and Application to Synthesis of an Azacarboline", *J. Heterocyclic Chem.*, 1994, 31, 1311–1315.

Porter et al., "Preparation of 6–phenyl–3–(5–tetrazolyl)pyridin=2 (H) –one Derivatives as Cyclic AMP–dependent Protein Kinase Agonists" *Chem. Abstr.*, 1992, 117(9), 90296n.

Ramalingnam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sánchez, H.I. et al., "Formal Total Synthesis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthesis Connections to the Aromati Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Thompson, W.J. and Gaudino, J., "A General Synthesis of 5–Arylnicotinates" *J. Org. Chem.*, 1984, *49*, 5237–5243.

Yeadon et al., "Mechanisms Contributing to Ozone–Induced Bronchial Hyperreactivity in Guinea Pigs", *Pulmonary Pharm.*, 1992, *5*, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, *51*, 4430–4435.

Sakakibara, K. et al., "Preparation of N–pyridyl–4–(benzyloxy)benzamides as Cardiotonics", *Chem. Abstr.*, 1988, *108*, no. 131583p.

Tsutsumi, K. et al., "Preparation of (Dialkoxyphosphinylmethyl) benzamides as Antihyperlipidemics", *Chem. Abstr.*, 1990, *113*, no. 6599a.

SUBSTITUTED 2-PYRIMIDINEAMINES AND PROCESSES FOR THEIR PREPARATION

This invention relates to a series of substituted 2-pyrimidineamines, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S. K., Hunter T., FASEB. J. 9, 576–596 (1995)]. The serine/threonine kinases include for example, protein kinase C isoforms [Newton A. C., J. Biol. Chem. 270, 28495–28498 (1995)] and a group of cyclin-dependent kinases such as cdc2 [Pines J., Trends in Biochemical Sciences 18, 195–197 (1995)]. The tyrosine kinases include membrane-spanning growth factor receptors such as the epidermal growth factor receptor [Iwashita S. and Kobayashi M. Cellular Signalling 4, 123–132 (1992)], and cytosolic non-receptor kinases such as $p56^{lck}$ $p59^{fyn}$ ZAP-70 and csk kinases [Chan C. et al Ann. Rev. Immunol. 12, 555–592 (1994)].

Inappropriately high protein kinase activity has been implicated in many diseases resulting from abnormal cellular function. This might arise either directly or indirectly, for example by failure of the proper control mechanisms for the kinase, related for example to mutation, overexpression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

We have now found a series of substituted 2-pyrimidineamines which are potent and selective inhibitors of protein kinases. The compounds are of use in the prophylaxis and treatment of immune diseases, hyperproliferative disorders and other diseases in which inappropriate protein kinase action is believed to have a role.

Thus, according to one aspect of the invention, we provide a compound of formula (1):

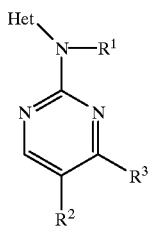

(1)

wherein Het is an optionally substituted heteroaromatic group; $R^1$ is a hydrogen atom or a straight or branched chain alkyl group; $R^2$ is a hydrogen or halogen atom or a group $-X^1-R^{2a}$ where $X^1$ is a direct bond or a linker atom or group, and $R^{2a}$ is an optionally substituted straight or branched chain alkyl, alkenyl or alkynyl group; $R^3$ is an optionally substituted aromatic or heteroaromatic group; and the salts, solvates, hydrates and N-oxides thereof.

In the compounds of formula (1), the group Het may be an optionally substituted $C_{1-13}$ heteroaromatic group, such as a $C_{1-9}$ heteroaromatic group, containing for example one, two, three or four heteroatoms selected from oxygen, sulphur or nitrogen atoms.

In general, Het may be for example a monocyclic heteroaromatic, or a bicyclic or tricyclic fused-ring heteroaromatic group. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms. Tricyclic heteroaromatic groups include for example ten- to fourteen-membered fused-ring heteroaromatic groups containing one, two or more heteroatoms selected from oxygen, sulphur or nitrogen atoms. The heteroaromatic group may be attached to the remainder of the compound of formula (1) through any of its ring carbon atoms.

Particular examples of heteroaromatic groups represented by Het include optionally substituted pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, indazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

Optional substituents which may be present on heteroaromatic groups represented by Het include one, two, three or more substituents, each represented by an atom or group $R^4$ or -Alk($R^4$)$_m$, where $R^4$ is a halogen atom, or an amino ($-NH_2$), substituted amino, nitro, cyano, hydroxyl ($-OH$), substituted hydroxyl, formyl, carboxyl ($-CO_2H$), esterified carboxyl, thiol ($-SH$), substituted thiol, $-COR^5$ [where $R^5$ is a -Alk($R^4$)$_m$, aryl or heteroaryl group], $CSR^5$, $-SO_3H$, $-SO_2R^5$, $-SO_2NH_2$, $-SO_2NHR^5$, $SO_2N[R^5]_2$, $-CONH_2$, $-CSNH_2$, $-CONHR^5$, $-CSNHR^5$, $-CON[R^5]_2$, $-CSN[R^5]_2$, $-NHSO_2H$, $-NHSO_2R^5$, $-N[SO_2R^5]_2$, $-NHSO_2NH_2$, $-NHSO_2NHR^5$, $-NHSO_2N[R^5]_2$, $-NHCOR^5$, $-NHCONH_2$, $-NHCONHR^5$, $-NHCON[R^5]_2$, $-NHCSR^5$, $-NHC(O)OR^5$, cycloalkyl, heterocycloalkyl, aryl or heteroaryl group; Alk is a straight or branched $C_{1-6}$ alkylene, $C_{2-6}$ alkenylene or $C_{2-6}$ alkynylene chain, optionally interrupted by one, two or three $-O-$ or $-S-$ atoms or groups selected from $S-(O)-$, $-S(O)_2-$ or $-N(R^6)-$ [where $R^6$ is a hydrogen atom or a straight or branched chain $C_{1-6}$ alkyl group]; and m is zero or an integer 1, 2 or 3.

When in the group -Alk($R^4$)$_m$ m is an integer 1, 2 or 3, it is to be understood that the substituent or substituents $R^4$ may be present on any suitable carbon atom in -Alk. Where more than one $R^4$ substituent is present these may be the same or different and may be present on the same or different atom in -Alk or in $R^4$ as appropriate. Thus for example, -Alk($R^4$)$_m$ may represent a $-CH(R^4)_2$ group, such as a $-CH(OH)Ar$ group where Ar is an aryl or heteroaryl group as defined below. Clearly, when m is zero and no substituent $R^4$ is present the alkylene, alkenylene or alkynylene chain represented by Alk becomes an alkyl, alkenyl or alkynyl group.

When $R^4$ is a substituted amino group it may be for example a group —$NHR^5$ [where $R^5$ is as defined above] or a group —$N[R^5]_2$ wherein each $R^5$ group is the same or different.

When $R^4$ is a halogen atom it may be for example a fluorine, chlorine, bromine, or iodine atom.

When $R^4$ is a substituted hydroxyl or substituted thiol group it may be for example a group —$OR^5$ or —$SR^5$ respectively.

Esterified carboxyl groups represented by the group $R^4$ include groups of formula —$CO_2Alk^1$ wherein $Alk^1$ is a straight or branched, optionally substituted $C_{1-8}$ alkyl group such as a methyl, ethyl, n-propyl, i-propyl, n-butyl, i-butyl, s-butyl or t-butyl group; a $C_{6-12}arylC_{1-8}alkyl$ group such as an optionally substituted benzyl, phenylethyl, phenylpropyl, 1-naphthylmethyl or 2-naphthylmethyl group; a $C_{6-12}aryl$ group such as an optionally substituted phenyl, 1-naphthyl or 2-naphthyl group; a $C_{6-12}aryloxyC_{1-8}alkyl$ group such as an optionally substituted phenyloxymethyl, phenyloxyethyl, 1-naphthyloxymethyl, or 2-naphthyloxymethyl group; an optionally substituted $C_{1-8}alkanoyloxyC_{1-8}alkyl$ group, such as a pivaloyloxymethyl, propionyloxyethyl or propionyloxypropyl group; or a $C_{6-12}aroyloxyC_{1-8}alkyl$ group such as an optionally substituted benzoyloxyethyl or benzoyloxypropyl group. Optional substituents present on the $Alk^1$ group include $R^4$ substituents described above.

When Alk is present in or as a substituent, it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —$S(O)_2$— or —$N(R^6)$— groups.

Cycloalkyl groups represented by the group $R^4$ include $C_{5-7}$ cycloalkyl groups such as cyclopentyl or cyclohexyl groups.

Heterocycloalkyl groups represented by the group $R^4$ include optionally substituted hetero$C_{3-6}$cycloalkyl groups containing one or two oxygen, sulphur or nitrogen atoms. Particular examples of such groups include optionally substituted azetidinyl, pyrrolidinyl, piperidinyl, piperazinyl, homopiperazinyl, morpholinyl or thiomorpholinyl groups. The heterocycloalkyl group may be attached to the remainder of the molecule through any of its ring carbon atoms or, where present, ring nitrogen atom. Optional substituents which may be present on groups of this type include one or two $C_{1-6}$ alkyl, e.g. methyl or ethyl, hydroxyl (—OH) hydroxy$C_{1-6}$alkyl, e.g. hydroxymethyl or hydroxyethyl, or $C_{1-6}$ alkoxy, e.g. methoxy or ethoxy groups. The substituent(s) may be present on any available ring carbon or nitrogen atom as appropriate.

Aryl and heteroaryl groups represented by the groups $R^4$, $R^5$ or Ar include for example optionally substituted monocyclic or bicyclic $C_{6-12}$ aromatic groups, e.g. phenyl groups, or $C_{1-9}$ heteroaromatic groups such as those described above in relation to the group Het.

Particularly useful atoms or groups represented by $R^4$ or $Alk(R^4)_m$ as appropriate include fluorine, chlorine, bromine or iodine atoms, or $C_{1-6}$alkyl, e.g. methyl or ethyl, $C_{1-6}$ alkylamino, e.g. methylamino or ethylamino, $C_{1-6}$hydroxyalkyl, e.g. hydroxymethyl or hydroxyethyl, $C_{1-6}$alkylthio e.g. methylthio or ethylthio, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, imido, such as phthalimido or naphthalimido, e.g. 1,8-naphthalimido, 1,1,3-trioxo-benzo[d]-thiazolidino, nitro, cyano, hydroxyl (—OH), formyl [HC(O)—], carboxyl (—$CO_2H$), —$CO_2Alk^1$ [where $Alk^1$ is as defined above], $C_{1-6}$ alkanoyl e.g. acetyl, thiol (—SH), thio$C_{1-6}$alkyl, e.g. thiomethyl or thioethyl, —$SC(NH_2+)NH_2$, sulphonyl (—$SO_3H$), $C_{1-6}$alkylsulphonyl, e.g. methyl-sulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, phenylaminosulphonylamino, aminocarbonylamino, $C_{1-6}$alkylaminocarbonylamino e.g. methylaminocarbonylamino or ethylaminocarbonylamino, $C_{1-6}$dialkylaminocarbonylamino, e.g. dimethylaminocarbonylamino or diethylaminocarbonylamino, phenylaminocarbonylamino, $C_{1-6}$alkanoylamino, e.g. acetylamino, $C_{1-6}$alkanoylamino$C_{1-6}$alkyl, e.g. acetylaminomethyl, $C_{1-6}$ alkoxycarbonylamino, e.g. methoxycarbonylamino, ethoxycarbonylamino or t-butoxycarbonylamino, or optionally substituted hetero$C_{3-6}$cycloalkyl, e.g. piperidinyl, piperazinyl, 3-methyl-1-piperazinyl, homopiperazinyl or morpholinyl groups.

Where desired, two $R^4$ or -$Alk(R^4)_m$ substituents may be linked together to form a cyclic group such as a cyclic ether, e.g. a $C_{2-6}$alkylenedioxy group such as ethylenedioxy.

It will be appreciated that where two or more $R^4$ or -$Alk(R^4)_m$ substituents are present, these need not necessarily be the same atoms and/or groups.

Particular examples of substituents which may be present on the heteroaromatic group Het include one, two or three substituents selected from fluorine, chlorine, bromine or iodine atoms or nitro, cyano, formyl, hydroxyl (—OH), thiol (—SH), amino (—$NH_2$), —$CH_3$, —$CH_2Hal$ (where Hal is a fluorine or chlorine atom), —$CH(Hal)_2$, —$C(Hal)_3$, —$CH_2OH$, —$CH_2CH_3$, —$(CH_2)_2CH_3$, —$CH(CH_3)_2$, —$(CH_2)_3CH_3$, —$CH(CH_3)CH_2CH_3$, —$CH_2CH(CH_3)_2$, —$C(CH_3)_3$, —$OCH_3$, —$SCH_3$, —$NHCH_3$, —$N(CH_3)_2$, —$OCH_2OCH_3$, —$OCH_2SCH_3$, —$O(CH_2)_2OCH_3$, —$(CH_2)_2OCH_2CH_3$, —$O(CH_2)_2NH_2$, —$O(CH_2)_2NHCH_3$, —$O(CH_2)_2N(CH_3)_2$, —$O(CH_2)_2OH$, —$CO_2H$, —$CO_2CH_3$, —$CO_2CH_2CH_3$, —$COCH_3$, —$CONH_2$, —$CONHCH_3$ or —$CON(CH_3)_2$ groups.

In the compounds of formula (1), when the group $R^1$ or the group $R^6$ [when present as —$N(R^6)$—] is a straight or branched chain alkyl group it may be for example a $C_{1-6}$ straight or branched chain alkyl group such as a methyl, ethyl, n-propyl or isopropyl group.

The group $R^2$ in compounds according to the invention may be for example a hydrogen or halogen atom such as a fluorine, chlorine, bromine or iodine atom, or a group —$X^1$—$R^{2a}$ where $X^1$ is a direct bond or linker atom or group, and $R^{2a}$ is an optionally substituted straight or branched chain alkyl, alkenyl or alkynyl group.

Linker atoms represented by $X^1$ when present in compounds of formula (1) include —O— or —S— atoms. When $X^1$ is a linker group it may be for example a —C(O)—, —C(S)—, —S(O)—, —S(O)$_2$—, —N(R$^7$)— [where R$^7$ is a hydrogen atom or a $C_{1-6}$ alkyl, e.g. methyl or ethyl, group], —CON(R$^7$)—, —OC(O)N(R$^7$)—, —CSN(R7)—, —N(R$^7$)CO—, —N(R$^7$)C(O)O—, —N(R$^7$)CS—, —SON(R$^7$), —SO$_2$N(R$^7$), —N(R$^7$)SO$_2$—, —N(R$^7$)CON(R$^7$)—, —N(R$^7$)CSN(R$^7$)—, —N(R$^7$)SON(R$^7$)— or —N(R$^7$)SO$_2$N(R$^7$) group.

When $R^{2a}$ is present in compounds of the invention it may be for example an optionally substituted straight or branched chain $C_{1-6}$ alkyl, e.g. $C_{1-3}$ alkyl, $C_{2-6}$ alkenyl e.g. $C_{2-4}$ alkenyl or $C_{2-6}$ alkynyl e.g. $C_{2-4}$ alkynyl group. Particular examples of such groups include optionally substituted —CH$_3$, —CH$_2$CH$_3$, —(CH$_2$)$_2$CH$_3$, —CH(CH$_3$)$_2$, —(CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$ or —(CH$_2$)$_2$CCH groups. The optional substituents which may be present on these groups include one, two, three or more substituents selected from halogen atoms, e.g. fluorine, chlorine, bromine or iodine atoms, or hydroxyl, $C_{1-6}$ alkoxy, e.g. methoxy or ethoxy, thiol, $C_{1-6}$ alkylthio, e.g. methylthio or ethylthio, amino $C_{1-6}$ alkylamino, e.g. methylamino or ethylamino, or $C_{1-6}$ dialkylamino, e.g. dimethylamino or diethylamino groups.

Aromatic groups represented by $R^3$ in compounds of formula (1) include for example optionally substituted monocyclic or bicyclic fused ring $C_{6-12}$ aromatic groups, such as optionally substituted phenyl, 1- or 2-naphthyl, or indenyl groups.

Heteroaromatic groups represented by $R^3$ include optionally substituted $C_{1-9}$ heteroaromatic groups containing for example one, two, three or four heteroatoms selected from oxygen, sulphur or nitrogen atoms. In general, the heteroaromatic groups may be for example optionally substituted monocyclic or bicyclic fused ring heteroaromatic groups such as those generally and particularly described above in relation to the group Het.

In general, when $R^3$ is a heteroaromatic group it is attached to the remainder of the molecule of formula (1) through any available ring nitrogen atom or, preferably, carbon atom.

Optional substituents which may be present on the aromatic or heteroaromatic group $R^3$ include one, two, three or more substituents each represented by the atom or group $R^8$ where $R^8$ represents an atom or group $R^4$ or -Alk(R$^4$)$_m$ as defined above in relation to the group Het. The substituent(s) $R^8$ may be attached to any available ring carbon or nitrogen atom in the group $R^3$. Where two or more $R^8$ substituents are present these need not necessarily be the same atoms and/or groups.

Particular $R^8$ substituents which may be present on the group $R^3$ in compounds of formula (1) include those identified above in relation to the atom or group $R^4$ or -Alk(R$^4$)$_m$ and especially include optionally substituted heteroC$_{3-6}$cycloalkyl groups such as those described above in relation to the group $R^4$. Particular examples of such groups include optionally substituted piperazinyl or homopiperazinyl groups, the optional substituents being those discussed previously in relation to heterocycloalkyl groups of this type.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that depending on the nature of the group Het and the substituents $R^2$ and $R^3$, the compounds of formula (1) may exist as geometrical isomers and/or may have one or more chiral centres so that enantiomers or diasteromers may exist. It is to be understood that the invention extends to all such isomers of the compounds of formula (1), and to mixtures thereof, including racemates.

In one preferred class of compounds of formula (1) $R^1$ is preferably a hydrogen atom. In these compounds, and in general in compounds of formula (1), $R^2$ is preferably a hydrogen atom or a group —X$^1$—R$^{2a}$ where $X^1$ is as defined for formula (1), and in particular is a direct bond, and $R^{2a}$ is an optionally substituted straight or branched chain $C_{1-6}$ alkyl group, or $R^2$ is especially a hydrogen atom.

In the compounds according to the invention the heteroaromatic group represented by Het is preferably an optionally substituted five- or six-membered monocyclic heteroaromatic group or a nine- or ten-membered fused-ring heteroaromatic group, each of said groups containing one or two oxygen, sulphur and/or nitrogen atoms. Particularly useful groups of these types include optionally substituted pyridyl, indolyl, benzimidazolyl, indazolyl, benzothiazolyl, quinolyl, isoquinolyl and benzoxazolyl groups. Optionally substituted quinolyl, indazolyl or benzothiazolyl groups are especially useful. The optional subsituent(s) may be any of those $R^4$ or -Alk(R$^4$)$_m$ atoms or groups generally or particularly described above.

In one general preference, $R^3$ in compounds of formula (1) is an optionally substituted heteroaromatic group containing one or two oxygen, sulphur and/or nitrogen atoms and is especially a monocyclic heteroaromatic group. Thus in particular $R^3$ may be an optionally substituted pyridyl group. The pyridyl group may in general be attached to the remainder of the compound of formula (1) through any available ring carbon atom and is in relation to that carbon atom, a 2-, 3- or 4-pyridyl group. Optionally substituted 3-pyridyl groups are especially useful. Optional substituents which may be present on these groups include one, two or three $R^8$ substituents as described in general and in particular above and hereinafter in the Examples. The $R^8$ substituent(s) may be attached in particular to any available ring carbon atom in the remainder of the group $R^3$.

A particularly useful group of compounds according to the invention has the formula (1) wherein Het is an optionally substituted nine- or ten-membered fused-ring heteroaromatic group containing one or two oxygen, sulphur and/or nitrogen atoms; $R^1$ and $R^2$ is each a hydrogen atom and $R^3$ is an optionally substituted monocyclic heteroaromatic group containing one or two oxygen, sulphur and/or nitrogen atoms.

In compounds of this type, Het is especially an optionally substituted pyridyl, indolyl, benzimidazolyl, benzothiazolyl, quinolyl, isoquinolyl or benzoxazolyl group. Optionally substituted quinolyl, indazolyl and benzothiazolyl groups are particularly preferred. The group $R^3$ is preferably an optionally substituted pyridyl group. The optional substituents which may be present on Het or $R^3$ groups include respectively those $R^4$ or $R^8$ substituents generally and particularly described above in relation to compounds of formula (1).

Particularly useful compounds according to the invention include those described hereinafter in the Examples and especially include:

N-(6-Benzothiazolyl)-4-(2-(1-piperazinyl)pyrid-5-yl)-2-pyrimidineamine;

N-(5-Indazolyl)-4-(2-(1-piperazinyl)pyrid-5-yl)-2-pyrimidineamine;

N-(6-Indazolyl-(-4-(2-(1-piperazinyl)pyrid-5-yl)-2-pyrimidineamine;

4-(2-(1-Piperazinyl)pyridin-5-yl)-N-(6-quinolyl)-2-pyrimidineamine;

N-(2-Methylthiobenzothiazol-6-yl)-4-(2-(1-piperazinyl)pyrid-5-yl)-2-pyrimidineamine;

and the salts, solvates and hydrates thereof.

Compounds according to the invention are potent and selective inhibitors of protein kinases as demonstrated by differential inhibition of enzymes such as EGFr kinase, $p56^{lck}$ kinase, ZAP-70 kinase, protein kinase C, Csk kinase and $p59^{fyn}$ kinase. The ability of the compounds to act in this way may be simply determined by employing tests such as those described in the Examples hereinafter.

The compounds according to the invention are thus of particular use in the prophylaxis and treatment of diseases in which inappropriate protein kinase action plays a role, for example in autoimmune diseases such as rheumatoid arthritis, multiple sclerosis, and systemic lupus erythematosus, in transplant rejection, in graft v host disease, in hyperproliferative disorders such as tumours, psoriasis, in pannus formation in rheumatoid arthritis, restenosis following angioplasty and atherosclerosis, and in diseases in which cells receive pro-inflammatory signals such as asthma, inflammatory bowel disease and pancreatitis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols Het, $R^1$—$R^3$, Alk, $Alk^1$ and Ar when used in the text or formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W.

in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a guanidine of formula (2):

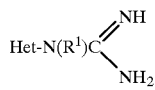
(2)

or a salt thereof with an enaminone of formula (3):

$$R^3COC(R^2)CHN(R^9)(R^{10})$$ (3)

where $R^9$ and $R^{10}$, which may be the same or different is each a $C_{1-6}$ alkyl group.

The reaction may be performed in a solvent, for example a protic solvent such as an alcohol, e.g. ethanol, methoxyethanol or propanol, optionally in the presence of a base e.g. an alkali metal base, such as sodium hydroxide or potassium carbonate, at an elevated temperature, e.g. the reflux temperature.

Salts of the compounds of formula (2) include acid salts such as inorganic acid salts e.g. hydrochlorides or nitrates.

Intermediate guanidines of formula (2) may be prepared by reaction of the corresponding amine HetNH$_2$ with cyanamide at an elevated temperature. The reaction may be performed in a solvent such as ethanol at an elevated temperature, e.g. up to the reflux temperature. Where it is desired to obtain a salt of a guanidine of formula (2), the reaction may be performed in the presence of a concentrated acid, e.g. hydrochloric or nitric acid.

The amines HetNH$_2$ are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below. The nitrobenzenes for this particular reaction are either known compounds or may be prepared using similar methods to those used for the preparation of the known compounds.

Intermediate enaminones of formula (3) are either known compounds or may be prepared by reaction of an acetyl derivative R$^3$COCH$_2$R$^2$ with an acetal (R$^9$)(R$^{10}$)NCH(OCH$_3$)$_2$ at an elevated temperature. The starting materials for this reaction are either known compounds or may be prepared by methods analogous to those used for the preparation of the known compounds.

In another process according to the invention, a compound of formula (1) may be prepared by displacement of a leaving atom or group in a pyrimidine of formula (4):

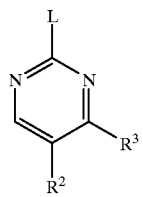
(4)

[where L is a leaving atom or group], with an amine HetNH$_2$.

The reaction may be performed at an elevated temperature, for example the reflux temperature, where necessary in the presence of a solvent, for example an alcohol, such as 2-ethoxyethanol or isopopanol or a substituted amide such as dimethylformamide, optionally in the presence of a base, for example an organic amine such as pyridine.

Particular examples of leaving atoms or groups represented by L in compounds of formula (4) include halogen atoms such as a chlorine or bromine atom, and sulphonyloxy groups, for example alkylsulphonyloxy groups such as a methylsulphonyloxy group.

Intermediate pyrimidines of formula (4) may be prepared by cross-coupling a pyrimidine of formula (5):

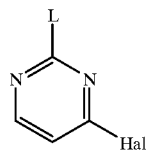
(5)

where Hal is a halogen atom such as a chlorine atom, with an organometallic reagent R$^3$MHal$^1$, where M is a metal atom, such as a zinc atom, and Hal$^1$ is a halogen atom, such as a chlorine atom.

The reaction may be carried out in the presence of a metal catalyst, for example a metal complex catalyst such as a palladium complex, e.g. tetrakis(triphenylphosphine) palladium, in a solvent such as an ether, e.g. a cyclic ether such as tetrahydrofuran, at an elevated temperature, e.g. the reflux temperature.

Organometallic reagents R$^3$MHal$^1$ may be prepared by conventional procedures, for example, where M is a zinc atom, by reaction of a halide R$^3$Hal$^2$ where Hal$^2$ is for example a bromine atom with tert-butyllithium at a low temperature e.g. around –100° C. followed by reaction with a zinc salt, e.g. zinc chloride at a low temperature, e.g. around –75° C. Both reactions may be carried out in a solvent such as an ether, e.g. tetrahydrofuran. Any reactive groups in R$^3$ not involved in this or the above-described coupling reaction may need to be in a protected form, the protecting group being removed prior to, during or subsequent to the displacement reaction involving the pyrimidines of formula (4). The starting halides R$^3$Hal$^2$ are either known compounds or may be prepared using analogous methods to those used for the preparation of the known compounds.

Compounds of formula (1) may also be prepared by interconversion of other compounds of formula (1) and it is to be understood that the invention extends to such interconversion processes. Thus, for example, standard substitution approaches employing for example alkylation, arylation, heteroarylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Het and/or $R^1$ or $R^3$ groups in compounds of formula (1). It will be appreciated that each of these reactions will only be possible where an appropriate functional group exists in a compound of formula (1).

Thus, for example alkylation, arylation or heteroarylation of a compound of formula (1) may be achieved by reaction of the compound with a reagent AlkL or ArL, where Alk is an alkyl group and Ar is an aryl or heteroaryl group as defined above in relation to compounds of formula (1) and L is a leaving atom or group as described above.

The alkylation or arylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 40° C.

In a variation of this process the leaving group L may be alternatively part of the compound of formula (1) and the reaction performed with an appropriate nucleophilic reagent at an elevated temperature. Particular nucleophilic reagents include cyclic amines, such as piperazine. Where appropriate the reaction may be performed in a solvent such as an alcohol, e.g. ethanol.

In another general example of an interconversion process, a compound of formula (1) may be acylated or thioacylated. The reaction may be performed for example with an acyl halide or anhydride in the presence of a base, such as a tertiary amine e.g. triethylamine in a solvent such as a halogenated hydrocarbon, e.g. dichloromethane at for example ambient temperature, or by reaction with a thioester in an inert solvent such as tetrahydrofuran at a low temperature such as around 0° C. The reaction is particularly suitable for use with compounds of formula (1) containing primary or secondary amino groups.

In a further general example of an interconversion process, a compound of formula (1) may be formylated, for example by reaction of the compound with a mixed anhydride $HCOOCOCH_3$ or with a mixture of formic acid and acetic anhydride.

Compounds of formula (1) may be prepared in another general interconversion reaction by sulphonylation, for example by reaction of the compound with a reagent AlkS(O)$_2$L, or ArS(O)$_2$L in the presence of a base, for example an inorganic base such as sodium hydride in a solvent such as an amide, e.g. a substituted amide such as dimethylformamide at for example ambient temperature. The reaction may in particular be performed with compounds of formula (1) possessing a primary or secondary amino group.

In further examples of interconversion reactions according to the invention compounds of formula (1) may be prepared from other compounds of formula (1) by modification of existing functional groups in the latter.

Thus in one example, ester groups —$CO_2Alk^1$ in compounds of formula (1) may be converted to the corresponding acid [—$CO_2H$] by acid- or base-catalysed hydrolysis or by catalytic hydrogenation depending on the nature of the group $Alk^1$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol. Catalytic hydrogenation may be carried out using for example hydrogen in the presence of a metal catalyst, for example palladium on a support such as carbon in a solvent such as an ether, e.g. tetrahydrofuran or an alcohol, e.g. methanol.

In a second example, —$OAlk^2$ [where $Alk^2$ represents an alkyl group such as a methyl group] groups in compounds of formula (1) may be cleaved to the corresponding alcohol —OH by reaction with boron tribromide in a solvent such as a halogenated hydrocarbon, e.g. dichloromethane at a low temperature, e.g. around −78° C.

In another example, alcohol —OH groups in compounds of formula (1) may be converted to a corresponding —OAlk or —OAr group by coupling with a reagent AlkOH or ArOH in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in compounds of formula (1) may be obtained, in another example, by reaction of a corresponding amine [—$NH_2$] with sulphamide in the presence of an organic base such as pyridine at an elevated temperature, e.g. the reflux temperature.

In another example of an interconversion process secondary amine groups in compounds of formula (1) may be alkylated using an alcohol, e.g. ethanol and catalytic hydrogenation, employing for example hydrogen in the presence of a metal catalyst such as palladium on a support such as carbon.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation as just described, or by chemical reduction using for example a metal, e.g. tin or iron, in the presence of an acid such as hydrochloric acid.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Where salts of compounds of formula (1) are desired, these may be prepared by conventional means, for example by reaction of a compound of formula (1) with an appropriate acid or base in a suitable solvent or mixture of solvents, e.g. an organic solvent such as an ether, e.g. diethylether, or an alcohol, e.g. ethanol.

The following Examples illustrate the invention. In the Examples all $^1$Hnmr were run at 300 MHz unless specified otherwise. All temperatures are in ° C.

INTERMEDIATE 1

5-Guanidino-2-methylbenzothiazole nitrate

5-Amino-2-methylbenzothiazole dihydrochloride (2.50 g, 10.54 mmol) was partitioned between dichloromethane and saturated aqueous sodium bicarbonate solution. The organic phase was dried ($MgSO_4$) and evaporated to afford the free base which was dissolved in ethanol (5 ml). A solution of cyanamide (660 mg, 15.71 mmol) in water (1 ml) was added followed by concentrated nitric acid (69%, 0.68 ml, 10.54 mmol) and the resulting mixture was refluxed for 18 h. The solid which formed on cooling to room temperature was collected and washed with cold ethanol then diethyl ether to give the title compound (1.36 g) as a beige solid m.p. 260–261° (dec.). $\delta_H$ (d$^6$ DMSO) 2.80 (3H, s), 7.26 (1H, m), 7.37 (4H, s), 7.78 (1H, s), 8.08 (1H, d, J 8.6 Hz) and 9.67 (1H, br s).

INTERMEDIATE 2

5-Guanidinoindole nitrate

A freshly prepared solution of cyanamide (0.48 g, 11.43 mmol) in water (1 ml) was added to a solution of 5-aminoindole (1.00 g, 7.56 mmol) in ethanol (5 ml). The mixture was treated with concentrated nitric acid (69%, 0.51 ml, 7.90 mmol) and then refluxed for 18 h. A further quantity of cyanamide (0.24 g, 5.71 mmol) was added and then heating continued for 5 h. The reaction mixture was cooled to room temperature and evaporated in vacuo. The residue was triturated with ethyl acetate and the resulting precipitate collected and washed with ethyl acetate then diethyl ether to give the title compound (1.67 g) as a brown solid m.p. 132–134°. $\delta_H$ (d$^6$ DMSO) 6.46 (1H, s), 6.92 (1H, dd, J 1.8, 8.5 Hz), 7.07 (4H, s), 7.43 (3H, m), 9.35 (1H, s), and 11.25 (1H, br s).

INTERMEDIATE 3

5-Guanidino-2-methoxypyridine dinitrate

From 5-amino-2-methoxypyridine (2.43 g, 19.60 mmol), using the same method as for the preparation of Intermediate 2 to afford the title compound (3.30 g) as a dark solid which was used without further purification in the next step. $\delta_H$ (d$^6$ DMSO) 3.85 (3H, s), 6.88 (1H, d, J 8.7 Hz), 7.33 (4H, s), 7.60 (1H, dd, J 2.6, 8.7 Hz), 8.07 (1H, d, J 2.6 Hz), 8.37 (1H, br s) and 9.37 (1H,s).

INTERMEDIATE 4

5-Bromo-2-(1-piperazinyl)pyridine

A mixture of 2,5-dibromopyridine (10.00 g, 42.21 mmol) and piperazine (7.98 g, 92.79 mmol) were heated as a melt at 125° for 3 h. On cooling to room temperature the mixture was triturated with 10% methanol-dichloromethane and filtered. The filtrate was evaporated and the residue subjected to column chromatography (silica, 5–8% methanol-dichloromethane) to afford the title compound (7.00 g) as a beige solid $\delta_H$ (CDCl$_3$) 2.75 (1H, br s), 2.97 (4H, m), 3.47 (4H, m), 6.52 (1H, d, J 9.1 Hz), 7.52 (1H, dd, J 9.1, 2.1 Hz), and 8.18 (1H, d, J 2.1 Hz).

INTERMEDIATE 5

5-Bromo-2-(4-tert-butoxycarbonylpiperazin-1-yl) pyridine

A suspension of Intermediate 4 (7.00 g, 28.91 mmol) in tetrahydrofuran (60 ml) at room temperature was treated with di-tert-butyldicarbonate (6.30 g, 28.90 mmol) and the resulting mixture stirred for 2 h, then evaporated and the crude product purified by recrystallisation (ethanol-water) to afford the title compound (8.76 g) as a beige solid m.p. 88–90°. $\delta_H$ (CDCl$_3$) 1.47 (9H, s), 3.50 (8H, m), 6.52 (1H, d, J 9.0 Hz), 7.52 (1H, dd, J 9.0, 2.5 Hz) and 8.18 (1H, d, J 2.5 Hz).

INTERMEDIATE 6

4-(2-(4-tert-butoxycarbonylpiperazin-1-yl)pyrid-5-yl)-2-chloropyrimidine

A solution of Intermediate 5 (6.00 g, 17.50 mmol) in anhydrous tetrahydrofuran (150 ml) was cooled to −100° (liquid nitrogen-diethyl ether) then treated dropwise with tert-butyllithium (22.0 ml of a 1.7M solution in pentane, 37.40 mmol) and the resulting thick yellow mixture stirred at −100° for 30 min. Zinc chloride (35.2 ml of a 0.5M solution in tetrahydrofuran, 17.60 mmol) was slowly added and the mixture stirred at −75° for 30 min then allowed to warm to room temperature whereupon 2,4-dichloropyrimidine (3.98 g, 26.71 mmol) and tetrakis (triphenylphosphine)palladium(0) (1.00 g, 0.86 mmol) were added. The resulting mixture was refluxed for 5 h then allowed to cool to room temperature. Saturated aqueous ammonium chloride was added and the mixture was extracted three times with ethyl acetate. The organic phase was washed with brine then dried (MgSO$_4$) and evaporated to give the crude product which was purified by recrystallisation (ethyl acetate-hexane) to afford the title compound (3.03 g) as a beige solid m.p. 182–183°. $\delta_H$ (CDCl$_3$) 1.48 (9H, s), 3.56 (4H, m), 3.69 (4H, m), 6.68 (1H, d, J 9.0 Hz), 7.49 (1H, d, J 5.4 Hz), 8.24 (1H, dd, J 2.5, 9.0 Hz), 8.49 (1H, d, J 5.4 Hz) and 8.82 (1H, d, J 2.5 Hz).

INTERMEDIATE 7

4-(2-(4-Benzyloxycarbonylpiperazin-1-yl)pyrid-5-yl)-2-chloropyrimidine

A solution of 4-(2-(4-tert-butoxycarbonylpiperazin-1-yl) pyrid-5-yl)-2-chloropyrimidine (8.00 g, 21.30 mmol) in dichloromethane (60 ml) was treated with trifluoroacetic acid and the resulting mixture stirred at room temperature for 2 h, then evaporated and reconcentrated four times from dichloromethane. The residue was suspended in a mixture of dichloromethane (150 ml) and saturated aqueous sodium bicarbonate (150 ml) then treated portionwise with benzyl chloroformate (4.00 g, 23.44 mmol) in dichloromethane (5 ml). The resulting mixture was stirred rapidly for 18 h then the organic phase was separated, dried (MgSO$_4$) and evaporated to give the crude product which was purified by recrystallisation (ethyl acetate-hexane) to afford the title compound (7.85 g) as an off-white solid m.p. 145–147°. $\delta_H$ (CDCl$_3$) 3.65–3.77 (8H, m), 5.18 (2H, s), 6.73 (1H, d, J 9.1 Hz), 7.36 (5H, m), 7.52 (1H, d, J 5.4 Hz), 8.31 (1H, dd, J 2.3, 8.1 Hz), 8.54 (1H, d, J 5.4 Hz) and 8.86 (1H, d, J 2.3 Hz).

INTERMEDIATE 8

2-Ethyl-5-nitrobenzoxazole

A solution of 2-amino-4-nitrophenol (2.00 g, 12.98 mmol) and triethyl orthopropionate (4.57 g, 25.95 mmol) in anhydrous ethanol (15 ml) was treated with p-toluenesulphonic acid (20 mg) and the resulting mixture refluxed for 3 h. On cooling to room temperature a precipitate formed which was filtered off and dried to afford the title compound (2.11 g) as a beige solid m.p. 88–90°. $\delta H$ (CDCl$_3$) 1.48 (3H, t, J 7.6 Hz), 3.02 (2H, q, J 7.6 Hz), 7.57 (1H, d, J 9.0 Hz), 8.27 (1H, dd, J 2.3, 9.0 Hz) and 8.55 (1H, d, J 2.3 Hz).

INTERMEDIATE 9

5-Amino-2-ethylbenzoxazole

A solution of Intermediate 8 (1.00 g, 5.21 mmol) and ammonium formate (1.64 g, 26.04 mmol) in ethanol (5 ml)

was treated with 10% palladium on charcoal (300 mg) and the resulting mixture stirred at room temperature for 3 h, then filtered through Celite®. The filtrate was evaporated and the residue partitioned between dichloromethane and aqueous sodium bicarbonate. The organic phase was dried (MgSO$_4$) and evaporated to afford the title compound (0.92 g) as a beige solid m.p. 85–87°. $\delta_H$ (CDCl$_3$) 1.42 (3H, t, J 7.6 Hz), 2.91 (2H, q, J 7.6 Hz), 3.50 (2H, br s), 6.70 (1H, dd, J 2.3, 8.5 Hz), 7.02 (1H, d, J 2.3 Hz) and 7.25 (1H, d, J 8.5 Hz).

EXAMPLE 1

4-(2-Chloropyrid-5-yl)-N-(2-methylbenzothiazol-5-yl)-2-pyrimidineamine

To a solution of Intermediate 1 (1.00 g, 4.20 mmol) and 1-(2-chloropyrid-5-yl)-3-dimethylamino-2-propen-1-one (0.88 g, 4.18 mmol) in propan-2-ol (10 ml) was added powdered sodium hydroxide (184 mg, 4.60 mmol) and the mixture refluxed for 18 h. The solid which formed on cooling to room temperature was collected and washed with propan-2-ol then water to afford the title compound (810 mg) as a beige solid m.p. 235–237°. $\delta_H$ (CDCl$_3$/CD$_3$OD, 1:1) 3.31(3H, s), 6.00 (1H, d, J 5.2 Hz), 6.27 (2H, m), 6.34 (1H, dd, J 2.0, 8.7 Hz), 6.51 (1H, d, J 8.7 Hz), 7.20 (2H, m) and 7.78 (1H, d, J 2.4 Hz).

The compounds of Example 2 and 3 were prepared by the same method:

EXAMPLE 2

4-(2-Chloropyrid-5-yl)-N-(5-indolyl)-2-pyrimidineamine

From Intermediate 2 (1.00 g, 4.21 mmol) to afford the title compound (795 mg) as an ochre solid m.p. 211–214° C. δH (d$^6$ DMSO) 6.38(1H, s), 7.28–7.39 (4H, m), 7.69 (1H, d, J 8.4 Hz), 7.95 (1H, s), 8.51 (2H, m), 9.14 (1H, d, J 2.2 Hz), 9.48 (1H, s) and 10.93 (1H, br s).

EXAMPLE 3

4-(2-Chloropyrid-5-yl)-N-(2-methoxypyrid-5-yl)-2-pyrimidineamine

From crude Intermediate 3 (1.40 g, 4.75 mmol) to afford the title compound (1.10 g) as a brown solid m.p. 203–205° C. $\delta_H$ (d$^6$DMSO) 3.83 (3H, s), 6.82 (1H, d, J 8.9 Hz), 7.47 (1H, d, J 5.2Hz), 7.71 (1H, d, J 8.3 Hz), 8.04 (1H, dd, J 2.7, 8.9 Hz), 8.50 (3H, m), 9.12 (1H, d, J 2.4 Hz) and 9.95 (1H, s).

EXAMPLE 4

N-(2-Methylbenzothiazol-5-yl)-4-(2-(1-piperazinyl)pyrid-5-yl)-2-pyrimidineamine A mixture of the compound of Example 1 (500 mg, 1.41 mmol) and piperazine (360 mg, 4.24 mmol) was heated as a melt at 140° for 2 h. On cooling to room temperature the mixture was triturated with dichloromethane and water then filtered and the residue subjected to column chromatography (silica, 5% methanol dichloromethane) to afford the title compound (331 mg) as a beige solid m.p. 209–211°. $\delta_H$ (d$^6$ DMSO) 2.78 (7H, m), 3.30 (1H, br s), 3.56 (4H, m), 6.92 (1H, d, J 9.2 Hz), 7.32 (1H, d, J 5.3 Hz), 7.70 (1H, dd, J 2.0, 8.7 Hz), 7.88 (1H, d, J 8.7 Hz), 8.25 (1H, dd, J 2.5, 9.2 Hz), 8.46 (1H, d, J 5.3), 8.59 (1H, d, J 1.9 Hz), 8.95 (1H, d, J 2.5 Hz) and 9.73 (1H, s).

The compounds of Examples 5 and 6 were prepared by the same method:

EXAMPLE 5

N-(5-Indolyl)-4-(2-(1-piperazinyl)pyrid-5-yl)-2-pyrimidineamine

From the compound of Example 2 (500 mg, 1.55 mmol) to afford the title compound (217 mg) as a pale yellow solid m.p. 245–250° (dec). $\delta_H$ (d$^6$ DMSO) 2.80 (4H, m), 3.38 (1H, br s), 3.50 (4H, m), 6.36 (1H, s), 6.92 (1H, d, J 9.0), 7.19 (1H, d, J 5.2 Hz), 7.27–7.40 (3H, m), 7.97 (1H, s), 8.24 (1H, d, J 9.0 Hz), 8.36 (1H, d, J 5.2 Hz), 8.90 (1H, s), 9.22 (1H, s) and 10.90 (1H, br s).

EXAMPLE 6

N-(2-Methoxypyrid-5-yl)-4-(2-(1-piperazinyl)pyrid-5-yl)-2-pyrimidineamine

From the compound of Example 3 (500 mg, 1.60 mmol) to afford the title compound (102 mg) as a beige solid m.p. 160–165°. $\delta_H$ (d$^6$ DMSO) 2.80 (4H, m), 3.57 (4H, m), 3.83 (3H, s), 6.81 (1H, d, J 8.9 Hz), 6.93 (1H, d, J 9.1 Hz), 7.28 (1H, d, J 5.3 Hz), 8.04 (1H, d, J 8.9 Hz), 8.21 (1H, d, J 7.0 Hz), 8.40 (1H, d, J 5.3 Hz), 8.58 (1H, s), 8.90 (1H, s) and 9.45 (1H, s).

EXAMPLE 7

N-(6-Benzothiazolyl)-4-(2-(1-piperazinyl)pyrid-5-yl)-2-pyrimidineamine hydrochloride A mixture of 6-aminobenzothiazole (156 mg, 1.06 mmol) and Intermediate 6 (200 mg, 0.53 mmol) in 2-ethoxyethanol (3 ml) was refluxed for 24 h. The solid which formed on cooling to room temperature was collected and washed with 2-ethoxyethanol then diethyl ether to give the title compound (170 mg) as a beige solid m.p. 310–312°. $\delta_H$ (d$^6$ DMSO) 3.19 (4H, m), 3.89 (4H, m), 7.08 (1H, d, J 9.1 Hz), 7.40 (1H, d, J 5.3 Hz), 7.83 (1H, dd, J 2.0, 8.9 Hz), 7.99 (1H, d, J 8.9 Hz), 8.35 (1H, dd, J 2.4, 9.1 Hz), 8.51 (1H, d, J 5.3 Hz), 8.72 (1H, d, J 2.0 Hz), 8.98 (1H, d, J 2.4 Hz), 9.19 (1H, s), 9.23 (2H, br s) and 9.88 (1H, s).

The compounds of Examples 8–10 were prepared by the same method as the compound of Example 7:

EXAMPLE 8

N-(5-Indazolyl)-4-(2-(1-piperazinyl)pyrid-5-yl)-2-pyrimidineamine hydrochloride From 5-aminoindazole (177 mg, 1.33 mmol) to afford the title compound (173 mg) as a beige solid m.p. >300°. $\delta_H$ (d$^6$DMSO) 3.91 (4H, m), 3.87 (4H, m), 7.06 (1H, d, J 9.0 Hz), 7.30 (1H, d, J 5.2 Hz), 7.47 (1H, d, J 8.9 Hz), 7.62 (1H, d, J 8.9 Hz), 7.99 (1H, s), 8.24 (1H, s), 8.33 (1H, dd, J 2.3, 9.0 Hz), 8.45 (1H, d, J 5.2 Hz), 8.96 (1H, d, J 2.3 Hz), 9.21 (2H, br s), 9.51 (1H, s), and 11.10 (1H, br s).

EXAMPLE 9

N-(6-Indazolyl)-4-(2-(1-piperazinyl)pyrid-5-yl)-2-pyrimidineamine hydrochloride From 6-aminoindazole (177 mg, 1.33 mmol) to afford the title compound (32 mg) as a brown solid m.p. 305–310°. $\delta_H$ (d$^6$DMSO) 3.19 (4H, m), 3.88 (4H, m), 7.07 (1H, d, J 8.8 Hz), 7.37 (2H, m), 7.61 (1H, d, J 8.8 Hz), 7.92 (1H, s), 8.31

(1H, s), 8.38 (1H, d, J 8.8Hz), 8.51 (1H, d, J 5.2 Hz), 9.01 (1H, s), 9.15 (2H, br s), 9.73 (1H, s) and 11.16 (1H, br s).

EXAMPLE 10

N-(6-Indolyl)-4-(2-(1-piperazinyl)pyrid-5-yl)-2-pyrimidineamine

From 6-aminoindole (141 mg, 1.07 mmol) to afford after column chromatography (silica, 0.88 ammonia solution-methanol-dichloromethane 1:10:89) the title compound (95 mg) as a yellow solid m.p. 201–203°. $\delta_H$ (d$^6$DMSO) 2.78 (4H, t, J 4.7 Hz), 3.55 (4H, t, J 4.7 Hz), 6.33 (1H, s), 6.89 (1H, d, J 9.1 Hz), 7.19–7.27 (3H, m), 7.41 (1H, d , J 8.5 Hz), 8.10 (1H, s), 8.28 (1H, d, J 9.1 Hz), 8.39 (1H, d, J 5.3 Hz), 8.93 (1H, s), 9.37 (1H, s) and 10.96 (1H, s).

EXAMPLE 11

N-(2-Methylbenzimidazol-5-yl)-4-(2-(1-piperazinyl)pyrid-5-yl)-2-pyrimidineamine

A solution of 4-(2-(4-tert-butoxycarbonylpiperazin-1-yl)pyrid-5-yl)-N-(2-methylbenzimidazol-5-yl)-2-pyrimidineamine (70 mg, 0.14 mmol) in a mixture of dichloromethane (5 ml) and methanol (3 ml) was treated with hydrogen chloride (5 ml of a 1M solution in diethyl ether, 5.00 mmol) then stirred for 18 h at room temperature. The precipitate which formed was collected by filtration then subjected to column chromatography (silica, 0.88 ammonia solution-methanol-dichloromethane, 1:5:94) to afford the title compound (19 mg) as a yellow solid m.p. 245–250°. $\delta_H$ (d$^6$DMSO) 2.45 (3H, s), 2.80 (4H, m), 3.38 (4H,m), 6.91 (1H, d, J 9.0 Hz), 7.24 (1H, d J 5.2 Hz), 7.35 (2H, s), 8.11 (1H, s), 8.25 (1H, m), 8.39 (1H, d, J 5.2 Hz), 8.93 (1H, d, J 2.2 Hz), 9.41 (1H, br s) and 11.50 (1H, br s).

The pyrimidineamine starting material for this reaction was prepared by treating a solution of Intermediate 6 (150 mg, 0.40 mmol) and 5-amino-2-methylbenzimidazole (117 mg, 0.80 mmol) in propan-2-ol (5 ml) with pyridine (0.5 ml) then refluxing for 4 days. The mixture was cooled to room temperature then evaporated and the residue subjected to column chromatography (silica, 2–10% methanol-dichloromethane) to afford 4-(2 -(4-tert-butoxycarbonylpiperazin-1-yl)pyrid-5-yl)-N-(2-methybenzimidazol-5-yl)-2-pyrimidineamine (63 mg) as a pale yellow solid m.p. 161–166°. $\delta_H$ (CDCl$_3$/CD$_3$OD) 1.44 (9H, s), 2.52 (3H, s), 2.98 (2H, br s), 3.51–3.61 (8H, m), 6.68 (1H, d, J 9.0 Hz), 6.97 (1H, d, J 5.3 Hz), 7.19 (1H, d, J 8.5 Hz), 7.42 (1H, d, J 8.5 Hz), 8.07 (1H, s), 8.13 (1H, dd, J 2.4, 9.0 Hz), 8.28 (1H, d, J 5.3 Hz) and 8.89 (1H, d, J 2.0 Hz).

EXAMPLE 12

N-(9-Ethylcarbazol-3-yl)-4-(2-(1-piperazinyl)pyrid-5-yl)-2-pyrimidine-amine

A solution of 4-(2-(4-tert-butoxycarbonylpiperazin-1-yl)pyrid-5-yl)-N-(9-ethylcarbazol-3-yl)-2-pyrimidineamine (65 mg, 0.12 mmol) in dichloromethane (2 ml) was treated with trifluoroacetic acid (2 ml). After 2h the mixture was evaporated and the residue reconcentrated five times from dichloromethane then three times from diethyl ether. The residue was subjected to column chromatography (silica, 0.88 ammonia solution-methanol-dichloromethane 1:5:94) to afford the title compound (28 mg) as a pale yellow solid m.p. 131–137°. $\delta_H$ (d$^6$DMSO) 1.31 (3H, t, J 7.1 Hz), 2.80 (4H, m), 3.56 (4H, m), 4.42 (2H, q, J 7.1 Hz), 6.93 (1H, d, J 9.1 Hz), 7.17 (1H, m), 7.25 (1H, d, J 5.3 Hz), 7.43 (1H, m), 7.55 (2H, m), 7.76 (1H, dd, J 2.9, 8.8 Hz), 8.03 (1H, d, J 7.4 Hz), 8.27 (1H, dd, J 2.1, 9.1 Hz), 8.41 (1H, d, J 5.3 Hz), 8.57 (1H, d, J 1.8 Hz), 8.95 (1H, d, J 2.1 Hz) and 9.45 (1H, s).

The pyrimidineamine starting material for this reaction was prepared by treating a solution of Intermediate 6 (180 mg, 0.48 mmol) and 3-amino-9-ethylcarbazole (299 mg, 1.44 mmol) in anhydrous dimethylformamide (2.5 ml) with pyridine (0.1 ml) then heating at 110° for 18 h. On cooling to room temperature the mixture was partitioned between ethyl acetate and brine, and the organic phase further washed four times with brine, dried (MgSO$_4$) and evaporated. The residue was subjected to column chromatography (silica, 1% methanol-dichloromethane) to afford 4-(2-(4-tert-butoxycarbonylpiperazin-1-yl)pyrid-5-yl)-N-(9-ethylcarbazol-3-yl)-2-pyrimidineamine (66 mg) as a brown oil. $\delta_H$ (CDCl$_3$) 1.44 (3H, t, J 7.2 Hz), 1.50 (9H, s), 3.56 (4H, m), 3.66 (4H, m), 4.37 (2H, q, J 7.2 Hz), 6.68 (1H, d J 9.0 Hz), 7.01 (1H, d, J 5.4 Hz), 7.20 (1H, dd, J 7.0, 7.0 Hz), 7.44 (4H, m), 7.67 (1H, dd, J 2.1, 8.7 Hz), 8.09 (1H, d, J 7.7 Hz), 8.24 (1H, dd, J 2.5, 9.0 Hz), 8.38 (1H, J 5.4 Hz), 8.40 (1H, d, J 2.1 Hz) and 8.90 (1H, d, J 2.5 Hz).

EXAMPLE 13

N-(5-Benzotriazolyl)-4-(2-(1-piperazinyl)pyrid-5-yl)-2-pyrimidineamine

A solution of N-(5-benzotriazolyl)-4-(2-(4-benzyloxycarbonylpiperazin-1-yl) pyrid-5-yl)-2-pyrimidineamine (200 mg, 0.39 mmol) and ammonium formate (400 mg, 6.35 mmol) in glacial acetic acid (5 ml) was treated with 10% palladium on charcoal (50 mg) and stirred for 24 h at room temperature. The mixture was filtered through Celite® washing with methanol, then evaporated and the residue subjected to column chromatography (silica, 0.88 ammonia-methanol-dichloromethane, 2:10:88) to afford the title compound (70 mg) as a white solid m.p. 280–283°. $\delta_H$ (d$^6$DMSO) 2.79 (4H, m), 3.57 (4H, m), 6.92 (1H, d, J 9.1 Hz), 7.37 (1H, d, J 5.3 Hz), 7.59 (1H, d, J 9.1 Hz), 7.85 (1H, d, J 9.1 Hz), 8.27 (1H, m), 8.48 (1H, d, J 5.3 Hz), 8.57 (1H, s), 8.96 (1H, s) and 9.86 (1H, s).

The pyrimidineamine starting material for this reaction was prepared by refluxing a solution of Intermediate 7 (410 mg, 1.00 mmol) and 5-amino-benzotriazole (147 mg, 1.10 mol) in 2-ethoxyethanol (5 ml) for 4 h, then allowing the reaction to cool to room temperature. The mixture was evaporated and the residue subjected to column chromatography (silica, 10% methanol-dichloromethane) to afford N-(5-benzotriazolyl)-4-(2-(4-benzyloxycarbonylpiperazin-1-yl)pyrid-5-yl)-2-pyrimidineamine (214 mg) as a pale yellow solid m.p. 247–249°. $\delta_H$ (d$^6$DMSO) 3.56 (4H, m), 3.70 (4H, m), 5.12 (2H, s), 6.98 (1H, d, J 9.2 Hz), 7.35 (6H, m), 7.59 (1H, d, J 9.2 Hz), 7.86 (1H, d, J 9.2 Hz), 8.30 (1H, m), 8.51 (1H, d, J 5.6 Hz),8.58 (1H, s), 8.99 (1H, s) and 9.86 (1H, s).

The compounds of Examples 14–16 were prepared by the same method as the compound of Example 13. In each case the pyrimidineamine starting material was prepared using the same method used for the pyrimidineamine starting material of the compound of Example 13.

EXAMPLE 14

4-(2-(1-Piperazinyl)pyridin-5-yl)-N-(6-quinolyl)-2-pyrimidineamine

From 4-(2-(4-benzyloxycarbonylpiperazin-1-yl)pyrid-5-yl)-N-(6-quinolyl)-2-pyrimidineamine (125 mg, 0.24 mmol)

to afford the title compound (30 mg) as a yellow solid m.p. 199–200°. δ$_H$ (d⁶DMSO) 2.78 (4H, m), 3.56 (4H, m), 6.96 (1H, d, J 9.0 Hz), 7.40 (1H, m), 7.41–7.46 (1H, m), 7.94 (1H, d, J 8.9 Hz), 8.03 (1H, d, J 8.9 Hz), 8.21 (1H, d, J 8.9 Hz), 8.30 (1H, d, J 9.0 Hz), 8.51 (1H, m), 8.58 (1H, s), 8.72 (1H, s), 8.96 (1H, s) and 9.93 (1H, s). 4-(2-(4-Benzyloxycarbonylpiperazin-1-yl)pyrid-5-yl)-N-(6-quinolyl)-2-pyrimidineamine was prepared from 6-aminoquinoline (159 mg, 1.10 mmol) to afford the title compound a pale beige solid (136 mg) m.p. 228–230°. δ$_H$ (CDCl₃) 3.53 (8H, m), 5.01 (2H, s), 6.63 (1H, d, J 9.0 Hz), 6.98 (1H, d, J 5.3 Hz), 7.18–7.28 (7H, m), 7.77 (1H, d, J 9.1 Hz), 7.84 (1H, d, J 9.1 Hz), 8.08 (2H, m), 8.27 (1H, d, J 5.3 Hz), 8.33 (1H, s), 8.52 (1H, d, J 2.8 Hz) and 8.70 (1H, s).

EXAMPLE 15

N-(2-Ethylbenzoxazol-5-yl)-4-(2-(1-piperazinyl)pyrid-5-yl)-2-pyrimidineamine

From 4-(2-(4-benzyloxycarbonylpiperazin-1-yl)pyrid-5-yl)-N-(2-ethylbenzoxazol-5-yl)-2-pyrimidineamine (100 mg, 0.19 mmol) to afford the title compound (71 mg) as a white solid m.p. 156–159°. δ$_H$ (CDCl₃/CD₃OD) 1.40 (3H, t, J 7.6 Hz), 2.93 (6H, m), 3.59 (4H, m), 6.69 (1H, d, J 8.4 Hz), 7.00 (1H, d, J 5.2 Hz), 7.38 (1H, d, J 8.8 Hz), 7.46 (1H, d, J 8.8 Hz), 8.07 (1H,s), 8.17 (1H, d, J 8.4 Hz), 8.29 (1H, d, J 5.2 Hz) and 8.80 (1H, s).

4-(2-(4-Benzyloxycarbonylpiperazin-1-yl)pyrid-5-yl)-N-(2-ethylbenzoxazol-5-yl)-2-pyrimidineamine was prepared from Intermediate 9 (111 mg, 0.69 mmol) to afford a beige solid (248 mg). δ$_H$ (CDCl₃) 1.46 (3H, t, J 7.6 Hz), 2.97 (2H, q, J 7.6 Hz), 3.69 (8H, m), 5.18 (2H, s), 6.71 (1H, d, J 10.0 Hz), 7.06 (1H, d, J 5.5 Hz), 7.40 (7H,m), 7.60 (1H, s), 8.12 (1H, s), 8.23 (1H, dd, J 2.3, 10.0 Hz), 8.34 (1H, d, J 5.5 Hz) and 8.88 (1H, d, J 2.3 Hz).

EXAMPLE 16

N-(4-Indolyl)-4-(2-(1-piperazinyl)pyrid-5-yl)-2-pyrimidineamine

From 4-(2-(4-benzyloxycarbonylpiperazin-1-yl)pyrid-5-yl)-N-(4-indolyl)-2-pyrimidineamine (74 mg, 0.15 mmol) to afford the title compound (35 mg), as a beige solid m.p. 224–226°. δ$_H$ (d⁶DMSO) 2.77 (4H, m), 3.54 (4H, m), 6.77 (1H, s), 6.89 (1H, d, J 9.0 Hz), 7.05 (2H, m), 7.26 (2H, m), 7.76 (1H, d, J 6.9 Hz), 8.23 (1H, d, J 9.0 Hz), 8.41 (1H, d J 5.3 Hz), 8.91 (1H, s), 9.05 (1H, s) and 11.02 (1H, s).

4-(2-(4-Benzyloxycarbonylpiperazin-1-yl)pyrid-5-yl)-N-(4-indolyl)-2-pyrimidineamine was prepared from 4-aminoindole hydrochloride (99 mg, 0.59 mmol) to afford a yellow foam (74 mg). δ$_H$ (CDCl₃) 3.65–3.71 (8H, m), 5.19 (2H, s), 6.66 (1H, s), 6.71 (1H, d, J 9.0 Hz), 7.05 (1H, d, J 5.4 Hz), 7.14–7.40 (8H, m), 7.67 (1H, br s), 8.05 (1H, d, J 7.6 Hz), 8.25 (1H, dd, J 2.4, 9.0 Hz), 8.32 (1H,s), 8.38 (1H, d, J 5.4 Hz) and 8.93 (1H, d, J 2.4 Hz).

EXAMPLE 17

N-(2-Ethylbenzoxazol-5-yl)-4-(2-(4-ethylpiperazin-1-yl)pyrid-5-yl)-2-pyrimidineamine A suspension of 4-(2-(4-benzyloxycarbonylpiperazin-1-yl)pyrid-5-yl)-N-(2-ethylbenzoxazol-5-yl)-2-pyrimidineamine (100 mg, 0.19 mmol) and 10% palladium on charcoal (30 mg) in ethanol (25 ml) was stirred under an atmosphere of hydrogen at 50° for 2 h, then filtered through Celite® and evaporated. The residue was subjected to column chromatography (silica, 0.88 ammonia solution-methanol-dichloromethane, 1:5:94) to afford the title compound (25 mg) as a white solid m.p. 174–176°. δ$_H$ (CDCl₃) 1.15 (3H, t, J 7.2 Hz), 1.45 (3H, t, J 7.6 Hz), 2.49 (2H, q, J 7.2 Hz), 2.58 (4H, m), 2.96 (2H, q, J 7.6 Hz), 3.71 (4H, m), 6.71 (1H, d, J 9.0 Hz), 7.04 (1H, d, J 5.3 Hz), 7.40 (1H, br s), 7.41 (1H, d, J 8.7 Hz), 7.49 (1H, dd, J 2.1, 8.7 Hz), 8.09 (1H, d, J 2.1 Hz), 8.20 (1H, dd, J 2.4, 9.0 Hz), 8.36 (1H, d, J 5.3 Hz) and 8.87 (1H, d, J 2.1 Hz).

EXAMPLE 18

4-(2-(1-Piperazinyl)pyridin-5-yl)-N-(6-quinolyl)-2-pyrimidineamine N-(2-Methylthiobenzothiazol-6-yl)-4-(2-(1-piperazinyl)pyrid-5-yl)-2-pyrimidineamine A solution of 4-(2-(4-benzyloxycarbonylpiperazin-1-yl)pyrid-5-yl)-N-(2-methylthiobenzothiazol-6-yl)-2-pyrimidineamine (120 mg, 0.20 mmol) in glacial acetic acid (10 ml) was treated with hydrogen bromide (3 ml of 40% aqueous solution) and heated at 55° for 2 h. The mixture was evaporated and the residue subjected to column chromatography (silica, 0.88 ammonia solution-methanol-dichloromethane, 1:10:89) to afford the title compound (29 mg) as a white solid m.p. 218–220°. δ$_H$ (d⁶DMSO) 2.77 (7H, m), 3.55 (4H, m), 5.73 (1H, s), 6.92 (1H, d, J 8.8 Hz), 7.32 (1H, d, J 5.3 Hz), 7.76 (2H, s), 8.25 (1H, d, J 8.8 Hz), 8.45 (1H, d, J 5.3 Hz), 8.56 (1H,s) and 8.92 (1H, s).

The pyrimidineamine starting material for this reaction was prepared using the same method described for the preparation of the starting material of Example 13:

4-(2-(4-Benzyloxycarbonylpiperazin-1-yl)pyrid-5-yl)-N-(2-methylthiobenzothiazol-6-yl)-2-pyrimidineamine was prepared from 6-amino-2-methylthiobenzothiazole (410 mg, 1.0 mmol) to afford after recrystallisation from ethanol-toluene a white solid (240 mg) m.p. 201–202°. δ$_H$ (CDCl₃) 2.78 (3H, s), 3.69 (8H, m), 5.19 (2H, s), 6.71 (1H, d, J 8.9 Hz), 7.06 (1H, d, J 5.4 Hz), 7.28–7.40 (6H, m), 7.45 (1H, d, J 5.4 Hz), 7.79 (1H, d, J 8.9 Hz), 8.19 (1H, d, J 8.9 Hz), 8.42 (2H, m) and 8.91 (1H, s).

EXAMPLE 19

N-(2-Benzimidazolyl)-4-(2-chloropyrid-5-yl)-2-pyrimidineamine

A solution of 2-guanidinobenzimidazole (0.83 g, 4.75 mmol) and 1-(2-chloropyrid-5-yl)-3-dimethylamino-2-propen-1-one (1.00 g, 4.75 mmol) in propan-2-ol (10 ml) was refluxed for 18 h. The solid which formed on cooling to room temperature was collected and washed with cold propan-2-ol to afford the title compound (205 mg) as a white solid m.p. 308–311°. δ$_H$ (d⁶DMSO) 7.06 (2H, m), 7.45 (2H, m), 7.69 (1H, d, J 5.3 Hz), 7.74 (1H, d, J 8.4 Hz), 8.59 (1H, dd, J 2.5, 8.4 Hz), 8.75 (1H, d, J 5.2 Hz), 9.21 (1H, d, J 1.9 Hz) and 11.30 (1H, br s).

EXAMPLE 20

N-(2-Benzimadazolyl)-4-(2-(1-piperazinyl)pyrid-5-yl)-2-pyrimidineamine

From N-(2-benzimidazolyl)-4-(2-chloropyrid-5-yl)-2-pyrimidineamine (200 mg, 0.62 mmol) using the same method used for the preparation of the compound of Example 4 to afford the title compound (108 mg) as a beige solid m.p. 285–287°. $\delta_H$ (d⁶DMSO) 2.78 (4H, m), 3.60 (4H, m), 6.93 (1H, d, J 9.1 Hz), 7.05 (2H,m), 7.44 (3H, m), 7.49 (1H, d, J 5.3 Hz), 8.28 (1H, dd, J 2.3, 9.1 Hz), 8.55 (1H, d, J 5.3 Hz), 8.96 (1H, d, J 2.3 Hz) and 11.50 (1H, br s).

Biological Activity

The following assays were used to demonstrate the activity and selectivity of compounds according to the invention:

p56$^{lck}$ Kinase Assay

The tyrosine kinase activity of p56$^{lck}$ was determined using a RR-src peptide (RRLIEDNEYTARG) and [γ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 µM ATP (0.5µ Ci[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 µl aliquot was removed, spotted onto a P-30 filtermat (Wallac, Milton Keynes, UK), and washed sequentially with 1% acetic acid and dH$_2$O to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK).

The dpm obtained, being directly proportional to the amount of $^{33}$P-RR-src produced by p56$^{lck}$, were used to determine the IC$_{50}$ for each compound. The IC$_{50}$ was defined as the concentration of compound required to reduce the production of $^{33}$P-RR-src by 50%.

In this test, the most active compounds according to the invention have IC$_{50}$ values of around 1 µM and below.

Zap-70 Kinase Assay

The tyrosine kinase activity of Zap-70 was determined using a capture assay based on that employed above for p56$^{lck}$. The RR-src peptide was replaced with polyGlu-Tyr (Sigma; Poole, UK) at a final concentration of 17 µg/ml. After addition of the stopped reaction to the filtermat, trichloroacetic acid 10% (w/v) was employed as the wash reagent instead of acetic acid and a final wash in absolute ethanol was also performed before scintillation counting. IC$_{50}$ values were determined as described above in the p56$^{lck}$ assay.

In this test the most active compounds of the invention have IC$_{50}$ values of around 500 nM and below.

EGFr Kinase Assay

The tyrosine kinase activity of the EGF receptor (EGFr) was determined using a similar methodology to the p56$^{lck}$ kinase assay, except that the RR-src peptide was replaced by a peptide substrate for EGFr obtained from Amersham International plc (Little Chalfont, UK) and used at the manufacturer's recommended concentration. IC$_{50}$ values were determined as described previously in the p56$^{lck}$ assay.

Protein Kinase C Assay

Inhibitor activity against protein kinase C (PKC) was determined using PKC obtained from Sigma Chemical Company (Poole, UK) and a commercially available assay system (Amersham International plc, Amersham, UK). Briefly, PKC catalyses the transfer of the γ-phosphate ($^{32}$p) of ATP to the threonine group on a peptide specific for PKC. Phosphorylated peptide is bound to phosphocellulose paper and subsequently quantified by scintillation counting. The inhibitor potency is expressed as either (i) the concentration required to inhibit 50% of the enzyme activity (IC$_{50}$) or (ii) the percentage inhibition achieved by 10 µM inhibitor.

In this test the most active compounds of the invention have IC$_{50}$ values of around 1 µM and below.

We claim:

1. A compound which is selected from the group consisting of:

N-(6-Benzothiazolyl)-4-(2-(1-piperazinyl)pyrid-5-yl)-2-pyrimidineamine;

N-(5-lndazolyl)-4-(2-(1-piperazinyl)pyrid-5-yl)-2-pyrimidineamine;

N-(6-lndazolyl-(-4-(2-(1-piperazinyl)pyrid-5-yl)-2-pyrimidineamine;

4-(2-(1-Piperazinyl)pyridin-5-yl)-N-(6-quinolyl)-2-pyrimidineamine;

N-(2-Methylthiobenzothiazol-6-yl)-4-(2-(1-piperazinyl)pyrid-5-yl)-2-pyrimidineamine;

and the salts, and hydrates thereof.

2. A pharmaceutical composition comprising, in combination with one or more pharmaceutically acceptable carriers, excipients or diluents, an effective amount of a compound according to claim 1.

3. A compound according to claim 1 which is N-(6-Benzothiazolyl)-4-(2-(1-piperazinyl)pyrid-5-yl)-2-pyrimidineamine; and the salts and hydrates thereof.

4. A compound according to claim 1 which is N-(5-Indazolyl)-4-(2-(1-piperazinyl)pyrid-5-yl)-2-pyrimidieamine; and the salts and hydrates thereof.

5. A compound according to claim 1 which is N-(6-Indazolyl-(4-(2-(1-piperazinyl)pyrid-5-yl)-2-pyrimidineamine; and the salts and hydrates thereof.

6. A compound according to claim 1 which is 4-(2-(1-Piperazinyl)pyridin-5-yl)-N-(6-quinolyl)-2-pyrimidineamine; and the salts and hydrates thereof.

7. A compound according to claim 1 which is N-(2-Methylthiobenzothiazol-6-yl)-4-(2-(1-piperazinyl)pyrid-5-yl)-2-pyrimidineamine; and the salts and hydrates thereof.

* * * * *